US006300350B1

(12) United States Patent
Belloni et al.

(10) Patent No.: US 6,300,350 B1
(45) Date of Patent: Oct. 9, 2001

(54) TREATMENT OF EMPHYSEMA USING RARY SELECTIVE RETINOID AGONISTS

(75) Inventors: Paula Nanette Belloni, Half Moon Bay, CA (US); Michael Klaus, Weil am Rhein (DE)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/691,967

(22) Filed: Oct. 18, 2000

Related U.S. Application Data

(60) Provisional application No. 60/160,415, filed on Oct. 19, 1999.

(51) Int. Cl.$^7$ ............... A61K 31/44; A61K 31/355; A61K 31/24; A61K 31/195; A61K 31/19
(52) U.S. Cl. ............... 514/350; 514/458; 514/538; 514/563; 514/569
(58) Field of Search .................... 514/350, 458, 514/538, 563, 569

(56) References Cited

U.S. PATENT DOCUMENTS

| | | |
|---|---|---|
| 5,130,335 | 7/1992 | Chandraratna et al. . |
| 5,498,795 | 3/1996 | Song et al. . |
| 5,700,836 | 12/1997 | Klaus et al. . |
| 5,726,191 | 3/1998 | Klaus et al. . |
| 5,760,084 | 6/1998 | Swann et al. . |

FOREIGN PATENT DOCUMENTS

| | | |
|---|---|---|
| WO 97/37648 | 10/1997 | (WO) . |
| WO 99/24024 A2 | 5/1999 | (WO) . |
| WO 99/45915 A1 | 9/1999 | (WO) . |
| WO 00/61182 | 10/2000 | (WO) . |
| WO 00/61232 | 10/2000 | (WO) . |
| WO 00/61233 | 10/2000 | (WO) . |

OTHER PUBLICATIONS

Kagechika, et al., Journal Med. Chemistry, vol. 32: 834–840 (1989) "Retinobenzoic Acids. 2. Structure–Activity Relationships of Chalcone–4–carboxylic Acids and Flavone–4'–carboxylic Acids".

Massaro & Massaro, American Journal Physiol., vol. 270, L305–L312 (1996) "Postnatal treatment with retinoic acid increases the number of pulmonary alveoli in rats".

Massaro & Massaro, Nature Medicine, vol. 3: 675–677 (1997) "Retinoic acid treatment abrogates elastase–induced pulmonary emphysema in rats".

NIH Report, Dated Apr. 17, 1998, RFA: HL–98–011, "Strategies to Augment Alveolization".

Primary Examiner—Raymond Henley, III
(74) Attorney, Agent, or Firm—Rohan Peries

(57) ABSTRACT

This invention provides methods of treating emphysema and other diseases associated with alveolar damage by treatment with an RARγ selective agonist. In another aspect, this invention provides methods of promoting tropoelastin gene expression and alveolar matrix repair by contacting the pulmonary intestitial fibroblast with an RAR agonist, preferably an RARγ selective agonist.

44 Claims, No Drawings

TREATMENT OF EMPHYSEMA USING RARγ SELECTIVE RETINOID AGONISTS

CROSS-REFERENCE TO RELATED APPLICATION

This application claims the benefit under 35 U.S.C. 119(e) of U.S. Provisional Application Ser. No. 60/160,415, filed Oct. 19, 1999, incorporated herein by reference in its entirety.

BACKGROUND OF THE INVENTION

1. Field of the Invention

This invention relates to methods of treating emphysema to regenerate functional alveoli using retinoic acid receptor agonists, in particular a retinoic acid receptor agonist that is RARγ selective.

2. Background Information

A. Emphysema

Chronic obstructive pulmonary disease (COPD) is a major cause of morbidity and mortality, ranking third and fourth as the leading cause of death in the European Union and North America respectively. COPD is characterized by reduced maximum expiratory flow that does not change over several months and persists for 2 or more consecutive years. Patients with the most severe form of COPD generally present with a significant degree of emphysema.

Emphysema is defined anatomically by permanent airspace enlargement distal to the terminal bronchioles, and it is characterized by gradual loss of lung recoil, alveolar destruction, decreased alveolar surface area and gas exchange, leading to a reduced FEV1 (American Thoracic Society: Am. J. Resp. and Critical Care 152: S77–S124, 1995). Impaired gas exchange and reduction in expiratory flow are characteristic physiological abnormalities from which emphysema patients suffer. The main symptom of severely affected emphysema patients is shortness of breath during minimal physical activity.

Although other potential environmental toxins may contribute, the most common cause of emphysema is cigarette smoking. These injurious agents activate destructive processes in the lung, including release of active proteases and free radical oxidants in excess of protective mechanisms. The uncontrolled release of active proteases creates an imbalance in protease/anti-protease levels in the lungs that leads to elastin matrix destruction, elastic recoil loss, tissue damage, and continuous lung function decline. The rate of this damage may be slowed by removing the injurious agents (for example, by quitting smoking); however, the damaged alveolar structures are not repaired and lung function is not regained.

B. Lung Development and Alveolar Septation

All-trans retinoic acid (ATRA) is a multifunctional modulator of cellular behavior, having the potential to alter both extracellular matrix metabolism and normal epithelial differentiation. In the lungs, ATRA has been shown to modulate various aspects of lung differentiation by interacting with specific retinoic acid receptors (RAR) that are selectively expressed temporally and spatially. Coordinated activation of RARβ and RARγ has been associated with lung branching, alveolization/septation and gene activation of tropoelastin in neonatal rats.

During alveolar septation, retinoic acid storage granules (retinyl-esters) increase in the fibroblastic mesenchyme surrounding alveolar walls (Liu et al; Am. J. Physiol. 265: L430–L437, 1993; McGowan et al Am. J. Physiol. 269: L463–L472, 1995), and RARγ expression in the lung peaks (Ong, D. E. and Chytil, F., Proc. Natl. Acad. of Sciences 73: 3976–3978, 1976; Grummer, M. A., Thet, L. and Zachman, R. D., Pediatr. Pulm. 17: 234–238, 1994). Depletion of these retinyl-ester stores parallels the deposition of new elastin matrix and sepation. In support of this concept, Massaro and Massaro (Massaro, D. and Massaro, G., Am. J. Physiol. 270, L305–L310, 1996) demonstrated that postnatal administration of retinoic acid increases the number of alveoli in rats. Treatment of newborn rat pups with dexamethasone inhibits the process of septation in the lungs. This effect can be overcome by supplemental treatment with retinoic acid. Furthermore, the capacity of dexamethasone to prevent the expression of CRBP and RARβ mRNA and subsequent alveolar septation in developing rat lung was abrogated by ATRA.

C. Retinoid Agonists in the Treatment of Emphysema.

Recent studies demonstrated that ATRA can induce formation of new alveoli and return elastic recoil to near normal in animal models of emphysema (Massaro, D. and Massaro, G., Nature Med. 3: 675–677, 1997; "Strategies to Augment Alveolization," National Heart, Lung, and Blood Institute, RFA: HL-98-011, 1998.). However the mechanism by which this occurs remains unclear.

D. Retinoids

Retinoids are a class of compounds structurally related to vitamin A, comprising natural and synthetic compounds. Several series of retinoids have been found clinically useful in the treatment of dermatological and oncological diseases. All-trans retinoic acid (ATRA) and its other naturally occurring retinoid analogs (9-cis retinioc acid, all-trans 3-4 didehydro retinioc acid, 4-oxo retinoic acid and retinol) are pleiotrophic regulatory compounds that modulate the structure and function of a wide variety of inflammatory, immune and structural cells. They are important regulators of epithelial cell proliferation, differentiation and morphogenesis in lung. Retinoids exert their biological effects through a series of nuclear receptors that are ligand inducible transcription factors belonging to the steroid/thyroid receptor superfamily.

The retinoid receptors are classified into two families, the retinoic acid receptors (RARs) and the retinoid X receptors (RXRs), each consisting of three distinct subtypes (α, β, and γ). Each subtype of the RAR gene family encodes a variable number of isoforms arising from differential splicing of two primary RNA transcripts. ATRA is the physiological hormone for the retinoic acid receptors and binds with approximately equal affinity to all the three RAR subtypes. ATRA does not bind to the RXR receptors; instead, for these receptors, 9-cis retinoic acid is the natural ligand.

In many non-pulmonary tissues, retinoids have anti-inflammatory effects, alter the progression of epithelial cell differentiation, and inhibit stromal cell matrix production. These properties have led to the development of topical retinoid therapeutics for dermatological disorders such as psoriasis, acne, and hypertrophic cutaneous scars. Other applications include the control of acute promyelocytic leukemia, adeno- and squamous cell carcinoma, and hepatic fibrosis. However, therapeutic use of retinoids outside of cancer is limited due to the relative toxicities observed with the naturally occurring retinoids, ATRA and 9-cis RA. These natural ligands are non-selective and, therefore, have pleiotrophic effects throughout the body, which are often toxic. Recently various retinoids have been described that interact selectively or specifically with the RAR or RXR receptors or with specific subtypes (α, β, γ) within a class. Using these novel retinoids, the transrepression of AP-1 and transactivation activities of retinoids have been separated.

(Li, J. J. et al, Cancer Research, 56: 483–489 (1996); Fanjul, A. et al., Nature, 372: 107–111 (1994); Schule R. et al., PNAS, 88: 6092–6096 (1991); Nagpal et al., Journal of Biological Chemistry 270: 923–927 (1995)). In addition, the receptor selective compounds have shown reduced general toxicity in vitro and in vivo. (Chandraratna, R., J. Am. Acad. Dermatology, 39: S149–S152, 1998; Look, J. et al., Am. J. Physiol. 269: E91–E98, 1995).

SUMMARY OF THE INVENTION

In one aspect, this invention provides methods of treating emphysema and associated pulmonary diseases by treatment of a mammal with an RARγ selective agonist. For this treatment systemic administration is a preferred mode of delivery. Use of retinoids that are at least RARγ selective and RARα sparing will promote repair without inducing adverse effects on levels of plasma triglycerides.

In another aspect, this invention provides methods of stimulating tropo-elastin gene expression in a human lung fibroblast by contacting the cell with an RARγ selective agonist.

DETAILED DESCRIPTION OF THE INVENTION

Definitions

As used herein, the term ($C_x$–$C_y$) alkyl means a linear or branched fully-saturated hydrocarbon radical having from x to y carbon atoms; a ($C_x$–$C_y$) fluoroalkyl is an alkyl radical, as defined above, in which one or more hydrogen atoms attached to the carbon backbone have been substituted with one or more fluorine atoms.

As used herein, the term ($C_x$–$C_y$) cycloalkyl means a fully saturated cyclic hydrocarbon radical of x to y ring carbon atoms and includes bicyclic, polycyclic and bridged ring systems, e.g., cyclopropyl, cyclopentyl, decalinyl, adamantyl and the like; the term ($C_x$–$C_y$) cyclofluoroalkyl is a cycloalkyl radical, as defined above, in which one or more hydrogen atoms attached to the carbon backbone have been substituted with one or more fluorine atoms.

As used herein, the term "E" denotes a stereochemical configuration about a carbon—carbon double bond such that the two hydrogen atoms are attached to different carbon atoms and are on opposite sides of the carbon—carbon double bond. The term "Z" denotes a stereochemical configuration about a carbon—carbon double bond such that the two hydrogen atoms are attached to different carbon atoms and are on the same side of the carbon—carbon double bond. (Pure Appl. Chem., 45, 13–30 (1976)).

As used herein, the term ED denotes effective dose and is used in connection with animal models. The term EC denotes effective concentration and is used in connection with in vitro models.

As used herein, the term "$ED_{50}$" of a retinoid for a retinoic acid receptor means the molar concentration of the retinoid in an animal model which transactivates the particular retinoic acid receptor under consideration by 50% of the maximum transactivation which can be obtained with that retinoid. As used herein, the term "$EC_{50}$" of a retinoid for a retinoic acid receptor means the molar concentration of the retinoid in an in vitro model which transactivates the particular retinoic acid receptor under consideration by 50% of the maximum transactivation which can be obtained with that retinoid.

As used herein, the term "retinoid" is any compound that is capable of transactivating any or all of the α, β, or γ RAR or RXR receptors with an $ED_{50}$ of 1000 nm or less.

As used herein, the term "transactivation" refers to the ability of a retinoid to activate the transcription of a gene where the gene transcription is initiated by the binding of a ligand to the particular retinoic acid receptor being tested, i.e., RARα, RARβ, or RARγ. Determining the ability of a compound to transactivate a retinoic acid receptor may be performed by methods known to those of skill in the art. Examples of such methods are found in Bernard et al., Biochem. Biophys. Res. Commun., 186: 977–983 (1992) and C. Apfel etal., Proc. Nat. Sci. Acad. (USA), 89: 7129–7133 (1992).

As used herein, the term "RARγ selective agonist" refers to a compound that is able to selectively bind to the RARγ receptor and promote RARγ activation. RARγ selective agonists will bind to the RARγ receptor at significantly lower concentrations (>10 fold selectivity, preferable 50 to 100 fold selectivity) than the RARα and RARβ receptors. The preferred activity profile will spare the activation of RARα receptors, leading to more selective biological responses.

As used herein, the term "RARγ/β selective agonist" is one that selectively binds to RARγ and RARβ receptors, promoting both RARγ and RARβ activation and sparing the activation of RARα receptors.

As used herein, the term "RAR agonist that is at least gamma selective and is RAR α sparing" is one that is RARγ selective or RARγ/β selective.

As used herein, the term "RAR pan agonist" is one that binds to RARα, RARβ, and RARγ receptors with similar affinity, promoting RARα, RARβ, and RARγ activation.

"Pro-drug" means any compound which releases an active parent drug in vivo when such prodrug is administered to a mammalian subject. Prodrugs are prepared by modifying functional groups present in the active drug in such a way that the modifications may be cleaved in vivo to release the parent compound. Prodrugs include compounds wherein a hydroxy group in the active drug is bonded to any group that may be cleaved in vivo to regenerate the free hydroxyl group. Examples of prodrugs include, but are not limited to esters (e.g., acetate, formate, and benzoate derivatives), carbamates (e.g., N,N-dimethylaminocarbonyl) and ethers of hydroxy functional groups in active drugs and the like. Such compounds are routinely made by one of skill in the art by acylating or etherifying the hydroxy group in the parent drug.

A "therapeutically effective amount" means the amount of a compound that, when administered to a mammal for treating or preventing a disease, is sufficient to effect such treatment or prevention for the disease. The "therapeutically effective amount" will vary depending on the compound, the disease and its severity, and the age, weight, etc., of the mammal to be treated.

The present inventors have discovered that RARγ selective agonists transactivate tropoelastin gene expression in human lung fibroblasts. Similarly, RARγ selective compounds were shown to promote the repair and/or regeneration of rat lung alveoli. Whereas RARγ selective retinoid agonists induced tropoelastin expression in human lung fibroblasts, neither RARβ nor RARα selective agonists did so. Consequently, one aspect of this invention is to promote the production of elastin containing extracellular matrix in a mammal by administering an agonist that is at least RARγ selective.

However, it will be recognized by one of skill in the art that the present invention encompasses the use of all RARγ selective agonists and is not limited to those RARγ selective agonists described in the above references or those presently known to the art. Generally, all compounds having at least RARγ selective agonist activity are useful for the methods of this invention.

One family of RARγ selective agonists useful in the methods described herein is described in U.S. Pat. No. 5,700,836, issued Dec. 23, 1997 and is represented by Formula I.

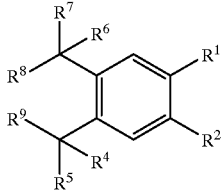

Formula I where $R^1$ is a residue of the formula

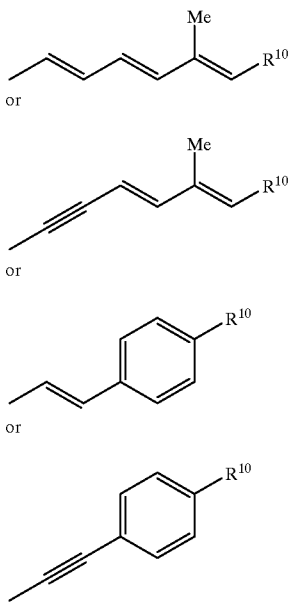

$R^2$ is $C_2$–$C_8$ alkanoyl, $C_2$–$C_8$ alkyl, $C_2$–$C_8$ alkenyl, $C_2$–$C_8$ alkynyl or —$OCH_2R^3$;

$R^3$ is hydrogen, $C_1$–$C_6$ alkyl, $C_2$–$C_6$ alkenyl or $C_2$–$C_6$ alkynyl;

$R^4$ to $R^9$ are each independently hydrogen or $C_1$–$C_6$ alkyl; or $R^8$ and $R^9$ together are $(CR^aR^b)_n$, $R^a$ and $R^b$ are independently hydrogen or $C_1$–$C_6$ alkyl, n is 1, 2 or 3 and $R^4$ to $R^7$ are the same as above;

$R^{10}$ is carboxyl, $C_{1-6}$ alkoxycarbonyl or mono- or di-($C_{1-6}$ alkyl)carbamoyl; and their pharmaceutically acceptable salts.

Particularly useful compounds within this family are compounds of Formula Ia or Ib:

Formula Ia

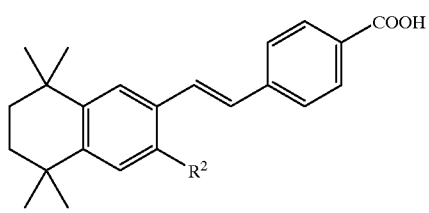

wherein $R^2$ is $C_2$–$C_8$ alkyl, —$OCH_2R^3$ or $C_2$–$C_8$ alkanoyl.

More specifically, $R^2$ is n-pentyl, n-hexyl, n-propoxy, n-pentoxy or n-hexanoyl.

Formula Ib

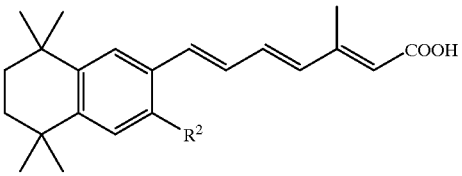

where $R^2$ is hexyl or n-pentoxy.

Another family of RARγ selective agonists useful in the methods described herein is described in U.S. Pat. No. 5,726,191, issued Mar. 10, 1998 and is represented by Formula II.

Formula II

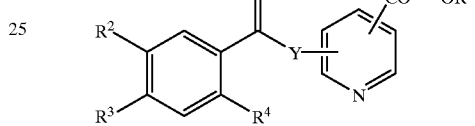

wherein;

$R^1$ is hydrogen or $C_1$–$C_6$ alkyl;

$R^2$ is $C_1$–$C_6$ alkyl or adamantyl;

$R^3$ is $C_1$–$C_6$ alkyl or hydroxy; or $R^2$ and $R^3$ taken together are —$(CR^6R^7)_n$— (where $R^6$ and $R^7$ are hydrogen or $C_1$–$C_6$ alkyl and n is 3, 4 or 5);

$R^4$ is $C_2$–$C_8$ alkanoyl, $C_2$–$C_8$ alkyl, $C_2$–$C_8$ alkenyl, $C_2$–$C_8$ alkynyl or —$OCH_2R^5$;

$R^5$ is $C_1$–$C_6$ alkyl, $C_2$–$C_6$ alkenyl or $C_2$–$C_6$ alkynyl;

Y is oxygen or sulfur; and their pharmaceutically acceptable salts.

Particularly useful compounds within this family are compounds of Formula IIa.

Formula IIa

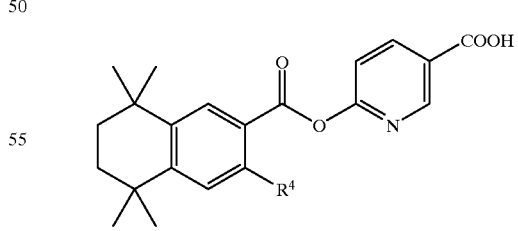

particularly those where $R^4$ is n-pentyl or n-hexyl.

A third family of RARγ selective agonists useful in the methods of this invention is that described in U.S. Pat. No. 5,498,795 issued Mar. 12, 1996 and is represented by Formula III.

Formula III

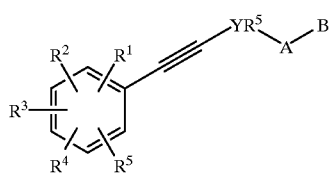

wherein $R^1$–$R^5$, A, B, and Y are as defined in U.S. Pat. No. 5,498,795.

A particularly useful compound in this family of RARγ selective agonists is that of Formula IIIa.

Formula IIIa

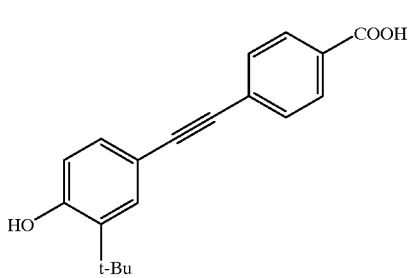

A fourth family of RARγ selective agonists useful in the methods of this invention is that described in U.S. Pat. No. 5,760,084 issued Jun. 2, 1998 and is represented by Formula IV.

Formula IV

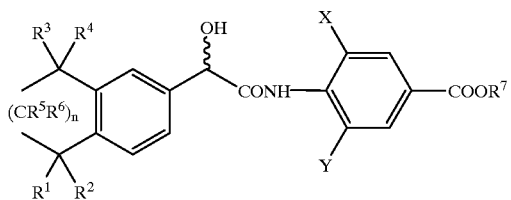

wherein $R^1$ through $R^7$, X, Y, and n are as defined in U.S. Pat. No. 5,760,084.

A particularly useful compound in this family of RARγ selective agonists is that of Formula IVa (BMS-961).

Formula IVa

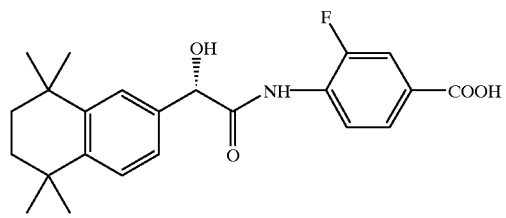

A fifth family of RARγ selective agonists useful in the methods of this invention is described in U.S. Pat. No. 5,130,335 issued Jul. 12, 1992 and U.S. Pat. No. 5,231,113 issued Jul. 27, 1993 and is represented by Formula V.

Formula V

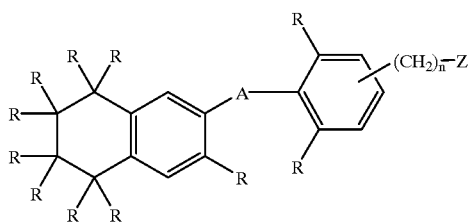

wherein R, A, Z, and n are as defined in U.S. Pat. No. 5,130,335.

A particularly useful compound in this family of RARγ selective agonists is that of Formula Va.

Formula Va

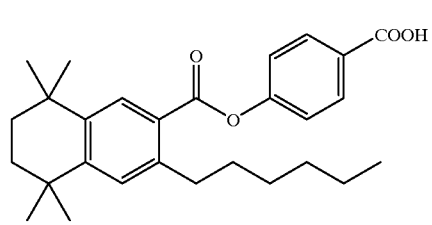

A sixth family of RARγ selective agonists useful in the methods of this invention is described in PCT Publication WO 97/37648 and French patent application FR2739557-A1, published Apr. 11, 1997 and is represented by Formula VI.

Formula VI

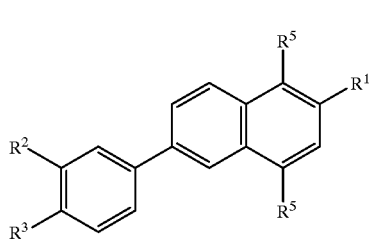

where $R^1$–$R^5$ are as described in WO 97/37648.

In particular, $R^1$ is C(O)R or $CH_2OH$ (where $R^6$ is hydroxy or $C_1$–$C_6$ alkoxy);

$R^2$ is hydrogen, $C_1$–$C_{15}$ alkyl, $C_1$–$C_6$ alkoxy or cycloaliphatic;

$R^3$ is hydrogen, hydroxy, $C_1$–$C_6$ alkyl, dihydroxy $C_1$–$C_6$ alkyl, $C_1$–$C_{10}$ alkoxy or cycloaliphatic; and $R^4$ and $R^5$ are independently hydrogen, hydroxy, $C_1$–$C_6$ alkyl, $C_1$–$C_6$ alkoxy.

A particularly useful compound in this family of RARγ selective agonists is that of Formula VIa (CD-437) and Formula VIb (CD-2247), described in Biochem. Biophys. Res. Commun. 179: 1554–1561 (1991), Biochem. Biophys. Res. Commun. 186: 977–984 (1992), and Int. J. Cancer 71: 497 (1997).

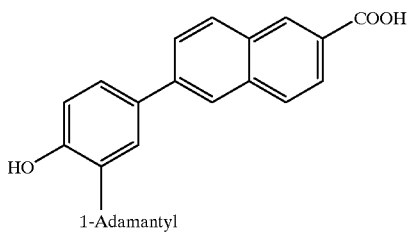

Formula VIa

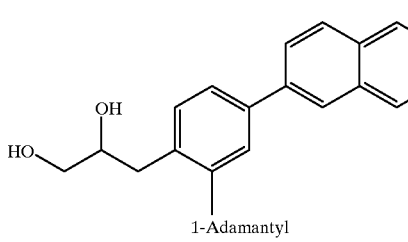

Formula VIb

Further compounds of interest are those of Formula VII, VIII, IX, X, and XI ((R) and (S) enantiomers) as described in Skin Pharmacol. 8: 292–299 (1995)).

Formula VII

Formula VIII

Formula X

Formula IX

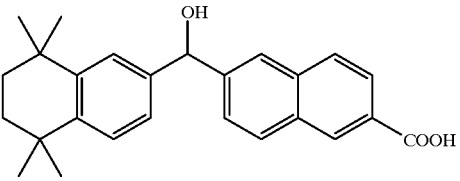

Formula XI

Other compounds useful in the methods of this invention are represented by Formula XII (J. Med. Chem. 39: 2411–2421 (1996) and Cancer Res. 55: 446–4451 (1995)).

Formula XII and Formula XIII and XIV (Cancer Letters, 115: 1–7 (1997)).

Formula XIII

Formula XIV

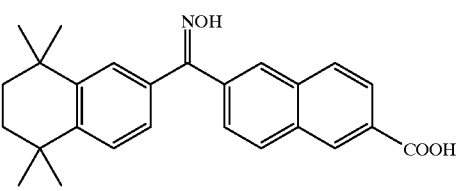

A further compound of interest is represented by Formula XV (J. Med. Chem. 32: 834–840 (1989) and Japanese patent publication 62/053981 (1987).

Formula XV

RARγ selective compounds should demonstrate a minimum 10 fold selectivity relative to RARα and RARβ in transactivation assays and preferably greater than 100 fold selectivity relative to RARα.

The RARγ agonist selectivity of a compound can be determined by routine ligand binding assays known to one of skill in the art such as described in C. Apfel et al., Proc. Nat. Sci. Acad. (USA), 89: 7129–7133 (1992); M. Teng et al., J. Med. Chem., 40: 2445–2451 (1997); and PCT Publication WO 96/30009.

Utility and Administration

The methods of treatment using RARγ selective agonists, as disclosed herein, may be used for promoting the repair of damaged alveoli and septation of new alveoli. As such, these methods are useful for treating diseases such as emphysema.

The particular dosage of a RAR agonist or an RARγ selective agonist required to promote alveolar repair/regeneration according to this invention will depend on the severity of the condition, the route of administration and related factors which will be decided by the attendant physician. Typically, the oral dosage will range between about 1.0 mg/kg of body weight per day (mg/kg/day) to 0.01 mg/kg/day, preferably from about 0.1 to about 0.05 mg/kg body weight per day. For a 50 kg human subject, the daily oral dose of active ingredient is from about 50 to about 0.5 mg, preferably from about 5 to about 2.5 mg. This dosage may be delivered in a conventional pharmaceutical composition by a single administration, by multiple applications, or via controlled release, as needed to achieve the most effective results. It is expected that local aerosol delivery of the drug to pulmonary airspaces would reduce the effective dose 10 to 100 fold (10 μg/kg/day to 0.1 μg/kg/day). Dosing will continue for as long as is medically indicated, which, depending on the severity of the disease, may range from a few weeks to several months.

Typically, a pharmaceutically acceptable composition, such as a salt, or prodrug of the RAR agonist in a pharmaceutically acceptable carrier or diluent is administered. In the context of the present invention, pharmaceutically acceptable salts include any chemically suitable salt known in the art of retinoids as applicable for administration to human patients. Examples of conventional salts known in the art include the alkali metal salts such as sodium and potassium salts, the alkaline earth metal salts such as calcium and magnesium salts, and ammonium and alkyl ammonium salts. Particularly preferred prodrug compositions of the RAR γ agonists include hydrolyzable ester derivatives such as aromatic and benzyl esters, or lower alkyl esters e.g., ethyl, t-butyl, cyclopentyl and the like.

Representative delivery regimens include oral, parenteral (including subcutaneous, intramuscular and intravenous), rectal, buccal (including sublingual), transdermal, pulmonary and intranasal. One method of pulmonary administration involves aerosolization of an aqueous solution of an RAR agonist. Aerosolized compositions may include the compound packaged in reverse micelles or liposomes. Other methods for pulmonary delivery include dry powder delivered with dry powder inhalant devices and liquid formulation of the retinoid agonist with polyethylene glycols or aqueous ethanol delivered with electrohydrodynamic inhalant devices. Typical pulmonary and respiratory delivery systems are described in U.S. Pat. Nos. 5,607,915, 5,238,683, 5,292,499, and 5,364,615, and "Aerosol delivery of liposomal ATRA to the lungs," Parthasarathy, R., Gilbert, B. M., and Mehta, K., Cancer Chemotherapy Pharmacol, 43: 277–283, 1999.

The treatment methods of this invention also include systemic administration of RARγ agonists in simultaneous or sequential combination with a further active ingredient for improving mucociliary clearance of airway mucus or reducing mucous viscosity. Representative active ingredients for improving mucociliary clearance include, for example, sodium channel blockers (e.g. amiloride) or antibiotics (e.g. duramycin, nisin or subtilin). Representative active ingredients for reducing mucous viscosity include N-acetylcysteine, homocysteine and phospholipids.

RARγ agonists will typically be administered as pharmaceutical compositions in admixture with a pharmaceutically acceptable, non-toxic carrier. As mentioned above, such compositions may be prepared for parenteral administration (subcutaneous, intramuscular or intravenous), particularly in the form of liquid solutions or suspensions; for oral or buccal administration, particularly in the form of tablets or capsules; for intranasal administration, particularly in the form of powders, nasal drops or aerosols; and for rectal or transdermal administration. Any conventional carrier material can be employed. The carrier material can be any organic or inorganic carrier material, such as water, gelatin, gum arabic, lactose, starch, magnesium stearate, talc, polyalkylene glycols, petroleum jelly and the like.

Liquid formulations for parenteral administration or for oral administration may contain as excipients sterile water or saline, alkylene glycols such as propylene glycol, polyalkylene glycols such as polyethylene glycol, oils of vegetable origin, hydrogenated naphthalenes and the like. They may employ slightly acidic buffers in pH ranges of about 4 to about 6. Suitable buffers include acetate, ascorbate and citrate at concentrations ranging from about 5 mM to about 50 mM. For oral administration, the formulation can be enhanced by the addition of bile salts or acylcarnitines.

Formulations for buccal administration may be solid and may contain as typical excipients sugars, calcium stearate, magnesium stearate, pregelatinated starch, and the like.

Solid forms for oral administration include tablets, hard and soft gelatin capsules, pills, sachets, powders, granules and the like. Each tablet, pill or sachet may contain from about 5 to about 200 mg of RARγ agonist, preferably from about 10 to about 50 mg. Preferred solid oral dosage forms include tablets, two-piece hard shell capsules and soft elastic gelatin (SEG) capsules. SEG capsules are of particular interest because they provide distinct advantages over the other two forms (see Seager, H., "Soft gelatin capsules: a solution to many tableting problems, "Pharmaceutical Technology, 9: (1985). Some of the advantages of using SEG capsules are: a) dose-content uniformity is optimized in SEG capsules because the drug is dissolved or dispersed in a liquid that can be dosed into the capsules accurately; b) drugs formulated as SEG capsules show good bioavailability because the drug is dissolved, solubilized or dispersed in an aqueous-miscible or oily liquid and therefore when released in the body the solutions dissolve or are emulsified to produce drug dispersions of high surface area; and c) degradation of drugs that are sensitive to oxidation during long-term storage is prevented because the dry shell.

Formulations for nasal administration may be solid and may contain excipients, for example, lactose or dextran, or may be aqueous or oily solutions for use in the form of nasal drops or metered spray. Particular nasal formulations include dry powders suitable for conventional dry powder inhalers (DPI's), liquid solutions or suspensions suitable for nebulization and propellant formulations suitable for use in metered dose inhalers (MDI's).

When formulated for nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like, in an amount in the range between about 0.2 and 15 weight percent, preferably between about 0.5 and 4 weight percent, most preferably about 2 weight percent.

Delivery of the compounds of the present invention to the subject over prolonged periods of time, for example, for periods of one week to one year, may be accomplished by a single administration of a controlled release system containing sufficient active ingredient for the desired release period. Various controlled release systems, such as monolithic or reservoir type microcapsules, depot implants, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

The following are representative pharmaceutical formulations for using RAR γ selective agonists as described herein for promoting elastin mediated matrix repair and alveolar septation.

Tablet formulation

The following ingredients are mixed intimately and pressed into single scored tablets. Quantity per tablet containing 1.0–50 mg active substance:

| Ingredient | Quantity per tablet, mg |
| --- | --- |
| RAR agonist | 10 |
| cornstarch | 50 |
| croscarmellose sodium | 25 |
| lactose | 120 |
| magnesium stearate | 5.0 |

Capsule formulation

The following ingredients are mixed intimately and loaded into a hard-shell gelatin capsule. Quantity per capsule containing 5 mg active substance:

| Ingredient | Quantity per capsule, mg |
| --- | --- |
| RAR agonist | 5 |
| lactose, spray-dried | 148 |
| magnesium stearate | 2 |

Suspension formulation

The following ingredients are mixed to form a suspension for oral administration:

| Ingredient | Amount |
| --- | --- |
| RAR agonist | 1.0–50 mg |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s.to 100 ml |

Injectable formulation

The following ingredients are mixed to form an injectable formulation:

| Ingredient | Amount |
| --- | --- |
| RAR agonist | 100 mg |
| sodium acetate buffer solution, 0.4 M | 2.0 ml |
| HCl (1N) or NaOH (1N) | q.s. to suitable pH |
| water (distilled, sterile) | q.s. to 20 ml |

Nasal formulation

The following ingredients are mixed to form a suspension for nasal administration:

| Ingredient | Amount |
| --- | --- |
| RAR agonist | 20 mg/ml |
| citric acid | 0.2 mg/ml |
| sodium citrate | 2.6 mg/ml |
| benzalkonium chloride | 0.2 mg/ml |
| sorbitol | 35 mg/ml |
| sodium taurocholate or glycocholate | 10 mg/ml |

The following preparations and examples are given to enable those skilled in the art to more clearly understand and to practice the present invention. They should not be considered as limiting the scope of the invention, but merely as being illustrative and representative thereof.

These examples utilized one or more of the RAR agonists contained in the following table

TABLE I

RAR Agonists Utilized in Examples

| RAR Agonist | Structure |
| --- | --- |
| 1 | 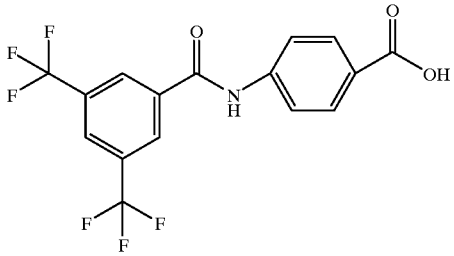 |
| 2 | 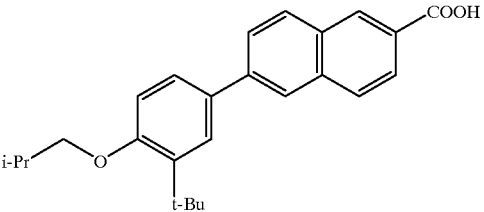 |
| 3 | 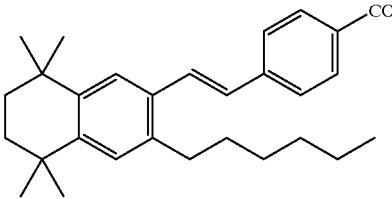 |
| 4 | 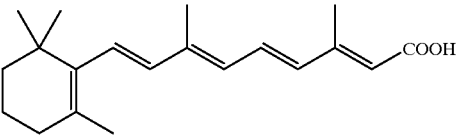 |

TABLE I-continued

RAR Agonists Utilized in Examples

| RAR Agonist | Structure |
|---|---|
| 5 | (tetrahydronaphthalene-styryl-COOH with pentanoyl group) |
| 6 | (chromanone-styryl-COOH) |
| 7 | Adamantyl (naphthyl-phenol-COOH) |
| 8 | (retinoic acid, COOH) |
| 9 | (tetrahydronaphthalene-CONH-phenyl-COOH) |
| 10 | (retinoid-COOH) |

EXAMPLE 1
RAR Transactivation of Steady State Tropoelastin Gene

Transactivation of the tropoelastin gene in normal human lung fibroblasts (CCD-16Lu) was performed as described below. Cells were grown to confluence at which time fresh media +/− ATRA or selective retiniod was added to the basal culture. ATRA and/or selective retinoids were used at a concentration of $1 \times 10^{-7}$ M. The cell layer was lysed using a guanidinium-based buffer (TRIZOL/Sigma) for RNA extraction and analysis. Amplification of tropoelastin and GAPDH RNA was performed by standard quantitative RT-PCR (TAQMAN, Perken/Elmer) using appropriate selective primers. Tropo-elastin gene expression was normalized to the expression of standard house-keeping gene (GAPDH).

Samples were run in triplicate. The results are shown below in Table II. These results demonstrate that ATRA (RAR Agonist 4) slightly induces tropoelastin gene induction compared to the control and that the RARγ selective agonist (RAR Agonist 3) markedly induces tropoelastin gene induction. However, the RARα and RARβ selective-agonists (RAR Agonists 1 and 2) did not induce the tropoelastin gene.

TABLE 11

RAR γ Drives Tropo-elastin Gene Expression in Human Lung Fibroblasts

| Treatment added to Cell Culture | | Transactivation $EC_{50}$ (nM) | Binding $IC_{50}$ (nM) | Tropo-elastin Expression (Elastin/ GAPDH) × $10^5$ |
|---|---|---|---|---|
| RAR Agonist 1 | α | 16.5 | 300 | |
| | β | 10000 | 10000 | 13.93 |
| | γ | 10000 | 10000 | |
| RAR Agonist 2 | α | 2000 | 1000 | |
| | β | 39 | 28 | 1.85 |
| | γ | 160 | 300 | |
| RAR Agonist 3 | α | 1000 | 2700 | |
| | β | 88 | 3000 | 68.58 |
| | γ | 15 | 210 | |
| ATRA | α | 6.7 | 14 | |
| RAR Agonist 4 | β | 3.8 | 14 | 35.50 |
| | γ | 2.5 | 14 | |
| Control | α | NA | | 30.90 |
| CCD-16Lu | β | NA | | |
| | γ | NA | | |

EXAMPLE 2
RAR Selective Agonists in Rat Lung

All-trans retinoic acid (ATRA) and RAR selective agonists were evaluated for their effects on alveolar repair in the rat model of elastase-induced emphysema (Massaro, G. and Massaro, D., Nature, Vol. 3 No. 6: 675–677 (1997)). Animals were divided into treatment groups of approximately eight. Lung inflammation and alveolar damage was induced in male Sprague Dawley rats by a single instillation of pancreatic elastase (porcine derived, Calbiochem) 2 U/gram body mass.

Three weeks post injury ATRA or a RAR selective agonist was dissolved in DMSO (20 mg/ml) and stored at −20 C. Fresh working stocks were prepared fresh daily by dilution in corn oil to a final concentration of 2 mg/ml. Animals treated with ATRA and RAR selective agonists (0.5 mg/Kg ip) were dosed once daily by intraperitoneal injection, starting 21 days post injury. Control groups were challenged with elastase and 21 days later treated with Vehicle (DMSO/PBS) for 14 days. Animals were sacrificed 24 hours after the last dose of by exsanguination under deep anesthesia. Blood was collected at time of exanguination for analysis of changes in blood chemistry from respective treatments.

The lungs were inflated with 10% neutral buffered formalin by intratracheal instillation at a constant rate (1 ml/gram body mass/min). The lung was excised and immersed in fixative for 24 hours prior to processing. Standard methods were used to prepare 5 um paraffin sections. Sections were stained with Hematoxylin and Eosin (H%E). Computerized Morphometric analysis was performed to determine the average alveolar size and alveolar number.

The results are shown below in Table III. These results demonstrate that ATRA (RAR Agonist 4) induces alveolar repair, reversing the alveolar destruction caused by treatment with elastase. RAR γ and RARγ/β selective agonists (RAR Agonists 3, 5, 6, and 7) markedly induce alveolar repair. However, RAR β and RAR α selective agonists (RAR Agonists 1, 2, and 9) do not induce alveolar repair.

In addition, light micrographs of lung sections were taken. Micrographs were taken of a normal rat lung, a rat lung damaged by elastase and then treated with RAR Agonist 1 (α selective), a rat lung damaged by elastase and then treated with RAR Agonist 2 (β selective), and a rat lung damaged by elastase and then treated with RAR Agonist 3 (γ selective). The micrographs revealed gross structural differences evident among the lungs receiving the three different treatments. When compared to the micrograph of the normal rat lung, the micrograph of the lung treated with the RAR γ selective agonist showed alveolar area similar to the normal rat lung. The micrograph of the lung treated with the RAR α selective agonist and the micrograph of the lung treated with the RAR β selective agonist did not reverse the change caused by elastase treatment.

Quantitation of triglycerides contained in rat plasma was performed after using established procedures in a contact clinical laboratory facility. Briefly, plasma triglycerides were converted to dihdroxyacetone and $H_2O_2$, by sequential treatment of plasma with lipase and glycerokinase according directions described by manufacturer of triglycerides/GPO kit (Boehringer Mannheim #1488872). $H_2O_2$ was quantitated calorimetrically in a Hitachi 911 Chemistry Analyzer. In rats normal triglyceride levels are 75–175 mg/dl.

The results are shown below in Table IV. Dosage was at 1 mg/kg/PO daily for two weeks. These results demonstrate that the RAR pan agonists (RAR Agonists 4 (ATRA), 8, and 10) cause triglyceride levels in rats to be either on the high end of normal or elevated. In contrast, the RARγ selective retinoids (RAR Agonists 3, 7, and 5) and RARγ/β selective retinoids (RAR Agonist 6) do not cause elevation in the triglyceride levels; for these RARα sparing retinoids, the triglyceride levels remain well within the middle to low end of the normal range. Therefore, it appears that RARα selective activity is linked to elevated triglyceride levels.

TABLE III

RAR Selective Agonists in Rat Lung

| Treatment Given | | Trans-activation $EC_{50}$ (nM) | Binding $IC_{50}$ (nM) | Alveolar Area | % Repair |
|---|---|---|---|---|---|
| Naïve (not treated | α | NA | | | |
| with Elastase) | β | NA | | 1637 +/− 153 | NA |
| | γ | NA | | | |
| Elastase + Vehicle | α | NA | | | |
| | β | NA | | 3570 +/− 319 | NA |
| | γ | NA | | | |
| ATRA | α | 6.8 | 14 | | |
| RAR Agonist 4 | β | 3.8 | 14 | 2607 +/− 191 | 50 |
| | γ | 2.5 | 14 | | |
| RAR Agonist 1 | α | 16.5 | 300 | | |
| | β | 10000 | 10000 | 3058 +/− 160 | <20 |
| | γ | 10000 | 10000 | | |
| RAR Agonist 2 | α | 2000 | 1000 | | |
| | β | 39 | 28 | 3653 +/− 550 | <20 |
| | γ | 160 | 300 | | |
| RAR Agonist 3 | α | 1000 | 2700 | | |
| | β | 88 | 3000 | 1929 +/− 150 | >70 |
| | γ | 15 | 210 | | |
| RAR Agonist 5 | α | 10000 | 2300 | | |
| | β | 10000 | 5400 | 2502 +/− 243 | 56 |
| | γ | 104 | 770 | | |
| RAR Agonist 6 | α | 10000 | 3100 | | |
| | β | 16 | 2100 | 1909 +/− 207 | >70 |
| | γ | 15 | 2410 | | |
| RAR Agonist 7 | γ | 2700 | 6500 | | |
| | β | 2300 | 4600 | 1817 +/− 241 | >70 |
| | γ | 9 | 310 | | |
| RAR Agonist 9 | α | 3 | 39 | | |
| | β | 25 | 870 | 3323 +/− 406 | <20 |
| | γ | 40 | 4500 | | |

EXAMPLE 3
Effects of RAR pan Agonist and RARγ and RARγ/β Selective Retinoid Agonists on Plasma Trigylceride Levels Experimental emphysema was induced in rats as described in Example 2. Three (3) weeks post injury animals were treated with vehicle (Capmul solution) or retinoids prepared in Capmul and dosed orally at 1, 3, and 10 mg/kg body weight. Animals were treated for 14 days prior to termination of study. Lung harvest and blood collection was performed as described in Example 2.

TABLE IV

RARγPromotes Alvelor Repair and Spares Triglycerides

| Treatment Given | Receptor Selectivity | % Repair | [Triglyceride] mg/dl |
|---|---|---|---|
| ATRA RAR Agonist 4 | α, β, γ | 37.6 | 182 |
| RAR Agonist 8 | α, β, γ | 57.1 | 178 |
| RAR Agonist 10 | α, β, γ | 58.3 | 273 |
| RAR Agonist 6 | γ, β | 39 | 140 |
| RAR Agonist 3 | γ | 73.7 | 92 |
| RAR Agonist 7 | γ | 66 | 114 |
| RAR Agonist 5 | γ | 40 | 119 |

EXAMPLE 4
Clinical Trial Study

Men and women enrolled in this study will be between the ages of 45–75, having a history of emphysema and will have ceased smoking for a period of at least 6 months prior to entry into the study. In addition the patient must present with minimum of 2 out of the 3 following pulmonary function criteria:

post bronchodialator TLC (total lung capacity)≧110% predicted (indicative of hyperinflation)

post bronchodialator FEV1 (forced expiratory volume) ≦70% predicted (indicative of moderate airflow obstruction).

DLCO (dilution lung carbon monoxide)≦65% predicted (indicative of moderate-to severe destruction of alveolar structures.

In addition the patients should have CT scan evidence of mild to moderate emphysema, adequate renal and hepatic function, and normal bone marrow. Patients will be excluded from the study having one or more of the following criteria: FEV1<0.8 liters, unexplained weight loss>10% usual weight per yea, recurrent lung infections>2 per year with sputum in excess of 3 tablespoons/day, bronchiectasis, unstable angina, hypertriglycerides>300 mg %, hypercholesteremia>220%, oral steroid dependency, concurrent medications known to interfere with P450 hepatic systems, acute or chronic liver disease of excessive alcohol consumption, or history of allergy to retinoids.

| Study Design | | | |
|---|---|---|---|
| Group | N | Dose | Regimen |
| A | 60 | placebo | 5 days/week |
| B1 | 60 | 1 mg/kg/ | 5 days/week |
| B2 | 60 | 1 mg/kg | 1 day/week |
| C1 | 60 | 0.1 mg/kg/ | 5 days/week |
| C2 | 60 | 0.1 mg/kg | 1 day/week |

All patients will be observed for a period of 3 months after completion of active treatment phase in order to assess residual lung improvement or toxicity. Pulmonary function testing (PFT) and system-based questionaires will be performed every 3 months. HRCT will be performed only at the beginning of screening and after completion of treatment. Individuals receiving high dose or potentially low dose of retinoid may demonstrate one or more of the following responses: reduction in rate of decline in FEV1 from 63 ml/year to 31 ml/year; show initial 5% improvement in FEV during first year of treatment; improvement in DLCo (5–10%); improvement in quality of life as determined by standard questionaire.

EXAMPLE 5
Determination of Pulmonary Gas Exchange

Pulmonary and arterial blood gases were determined in elastase damaged rats±retinoid treatment prior to termination of study. Rats were placed under deep anesthesia using pentobarbital (50 mg/kg, i.p. and a tracheal cannula (PE 240) was inserted. The rats were artificially ventilated (f=90, TV=approx 0.5 ml/100 g BW) using a small animal respiratory pump (Harvard). For each rat, the pump parameters were adjusted to establish an arterial $CO_2$ level for the pulmonary artery ($PCO_2$) of 30–35 torr. Arterial blood samples (approx 0.2 ml) were taken from the abdominal aorta (AO2) and immediately analyzed by pHOx blood gas. Data are presented as percent (%) recovery relative to elastase +vehicle treated rats.

As shown below, treatment of elastase-damaged rats with retinoids improved gas exchange. In particular, RARg selective Agonist 3 was more effective and more potent than the pan agonist (ATRA). This result is consistent with the effects on the structural repair of alveoli in the earlier Examples. Improved gas exchange correlates with decreasing the shortness of breath associated with emphysema. Thus, treatment of a patient with an RAR-gamma selective agonist will result in the alleviation of one of emphsema's major symptoms.

| Compound | Dose mg/kg | PCO2 | PO2 | AO2 |
|---|---|---|---|---|
| ATRA | 3.0 | 69.1 | 49.1 | 74.8 |
| Agonist 4 | | | | |
| RAR Agonist 3 | 0.01 | 84.6 | 49.8 | 100 |

The foregoing invention has been described in some detail by way of illustration and example, for the purposes of clarity and understanding. It will be obvious to one of ordinary skill in the art that changes and modifications may be practiced within the scope of the appended claims. Therefore, it is to be understood that the above description is intended to be illustrative and not restrictive. The scope of the invention should, therefore, be determined with reference to the following appended claims, along with the full scope of equivalents to which such claims are entitled.

The patents, patent applications and publications cited in this application are hereby incorporated by reference in their entirety for all purposes to the same extent as if each individual patent, patent application or publication were so individually denoted.

What is claimed is:

1. A method of treating emphysema in a mammal by administering to the mammal an RAR agonist that is at least gamma selective and is RARα sparing.

2. The method of claim 1, wherein the RAR agonist is an RARγ/β selective agonist.

3. The method of claim 1, wherein the RAR agonist is an RARγ selective agonist.

4. The method of claim 3, wherein the RARγ selective agonist binds to the RARγ receptor and transactivates with an $EC_{50}$ of at least 200 nM.

5. The method of claim 3, wherein the selectivity of the RARγ selective agonist for the RARγ receptor is at least 20 fold relative to the RARα and RARβ receptors.

6. The method of claim 3, wherein the RAR agonist is selected from compounds of Formula I:

Formula I

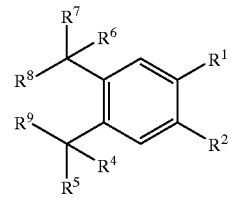

where $R^1$ is a residue of the formula

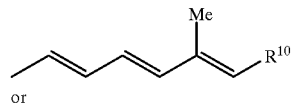

or

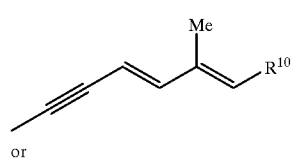

or

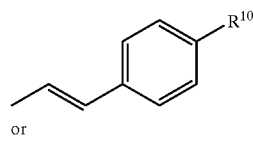

or

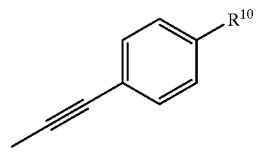

$R^2$ is $C_2$–$C_8$ alkanoyl, $C_2$–$C_8$ alkyl, $C_2$–$C_8$ alkenyl, $C_2$–$C_8$ alkynyl or —$OCH_2R^3$;

$R^3$ is hydrogen, $C_1$–$C_6$ alkyl, $C_2$–$C_6$ alkenyl or $C_2$–$C_6$ alkynyl;

$R^4$ to $R^9$ are each independently hydrogen or $C_1$–$C_6$ alkyl;

or $R^8$ and $R^9$ together are $(CR^aR^b)_n$, $R^a$ and $R^b$ are independently hydrogen or $C_1$–$C_6$ alkyl, n is 1, 2 or 3 and $R^4$ to $R^7$ are the same as above;

$R^{10}$ is carboxyl, $C_{1-6}$ alkoxycarbonyl or mono- or di-($C_{1-6}$ alkyl)carbamoyl; and their pharmaceutically acceptable salts.

7. The method of claim 3, wherein the RAR agonist is selected from compounds of Formula II:

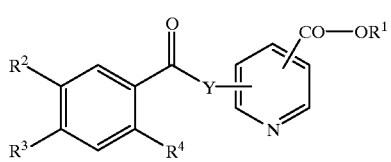

Formula II wherein;

$R^1$ is hydrogen or $C_1$–$C_6$ alkyl;

$R^2$ is $C_1$–$C_6$ alkyl or adamantyl;

$R^3$ is $C_1$–$C_6$ alkyl or hydroxy; or $R^2$ and $R^3$ taken together are —$(CR^6R^7)_n$,— (where $R^6$ and $R^7$ are hydrogen or $C_1$–$C_6$ alkyl and n is 3, 4 or 5);

$R^4$ is $C_2$–$C_8$ alkanoyl, $C_2$–$C_8$ alkyl, $C_2$–$C_8$ alkenyl, $C_2$–$C_8$ alkynyl or —$OCH_2R^5$;

$R^5$ is $C_1$–$C_6$ alkyl, $C_2$–$C_6$ alkenyl or $C_2$–$C_6$ alkynyl;

Y is oxygen or sulfur; and their pharmaceutically acceptable salts.

8. The method of claim 3, wherein the RAR agonist is selected from compounds of Formula III:

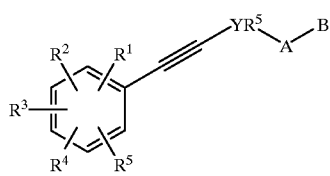

Formula III wherein $R^1$–$R^3$ and $R^5$ are independently hydrogen, lower alkyl of 1 to 6 carbons, branched chain alkyl or cycloalkyl of 3 to 15 carbons, lower alkyl substituted cycloalkyl of 3 to 15 carbons;

$R^4$ is lower alkyl of 1 to 6 carbons, branched chain alkyl or cycloalkyl of 3 to 15 carbons, or lower alkyl substituted cycloalkyl of 3 to 15 carbons;

X is S or O;

Y is a phenyl group, or heteroaryl selected from a group consisting of pyridyl, thienyl, furyl, pyridazinyl, pirimidinyl, pyrazinyl, thiazolyl, imidazolyl, and oxazolyl, said groups being substituted with the R5 group defined above;

A is $(CH_2)_n$ where n is 0 to 5, lower branched chain alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds;

B is hydrogen, COOH or a pharmacetically acceptable salt thereof, $COOR^8$, $CONR^9R^{10}$, —$CH_2OH$, $CH_2OR^{11}$, $CH_2OCOR^{11}$, CHO, $CH(OR^{12})_2$, $CHOR^{13}O$, —$COR^7$, $CR^7(OR^{12})_2$, or $CR^7OR^{13}O$, where $R^7$ is an alkyl, cycloalkyl, or alkenyl group containing 1 to 5 carbons, $R^8$ is an alkyl group of 1 to 10 carbons, or a cycloalkyl group of 5 to 10 carbons, or $R^8$ is phenyl or lower alkylphenyl, $R^9$ and $R^{10}$ independently are hydrogen, an alkyl grop of 1 to 10 carbons, or a cycloalkyl group of 5 to 10 carbons, or phenyl or lower alkylphenyl, $R^{11}$ is a lower alkyl, phenyl or lower alkylphenyl, $R^{12}$ is lower alkyl, and $R^{13}$ is divalent alkyl radical of 2 to 5 carbons.

9. The method of claim 3, wherein the RAR agonist is selected from compounds of Formula IV:

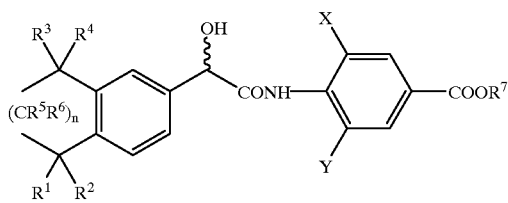

Formula IV wherein

X is F, Cl, OH, or $CH_3$;

Y is H or F;

$R^1$ through R are each independently hydrogen or $C_1$ to $C_6$ alkyl;

n is an integer of 1 to 4; and $R^7$ is hydrogen or a carboxyl-protecting group; and pharmaceutically acceptable salts thereof.

10. The method of claim 3, wherein the RAR agonist is selected from compounds of Formula V

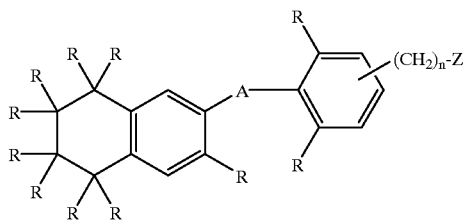

Formula IV wherein the R groups are independently hydrogen or lower alkyl;

A is —C(O)O—, —OC(O)—, —C(O)S—, or SC(O)—;

n is O to 5; and

Z is H, —COB, —OE, —CHO or an acetal derivative thereof, or —$COR^3$ wherein

B is —$OR^1$ wherein $R^1$ is an ester-forming group, or B is —$N(R)_2$ wherein R is hyrogen or lower alkyl;

E is hydrogen, an ether-forming group, or —$COR^2$ where $R^2$ is hydrogen, lower alkyl, phenyl, or lower alkyl phenyl;

$R^3$ is —$(CH_2)_mCH_3$ wherein m is 0 to 4 and the sum of n and m does not exceed 4.

11. The method of claim 3, wherein the RAR agonist is selected from compounds of Formula VI

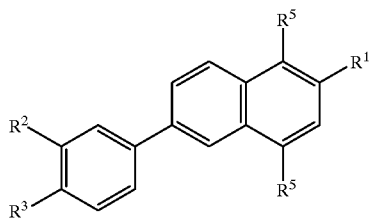

Formula VI wherein

R[1] is C(O)R[6] or CH$_2$OH (where R[6] is hydroxy or C$_1$–C$_6$ alkoxy);

R[2] is hydrogen C$_1$–C$_{15}$ alkyl, C$_1$–C$_6$ alkoxy or cycloaliphatic;

R[3] is hydrogen, hydroxy, C$_1$–C$_6$ alkyl, dihydroxy C$_1$–C$_6$ alkyl, C$_1$–C$_{10}$ alkoxy or cycloaliphatic; and R[4] and R[5] are independently hydrogen, hydroxy, C$_1$C$_6$ alkyl, C$_1$–C$_6$ alkoxy.

12. The method of claim 6, wherein the RAR agonist is a compound of Formula VII:

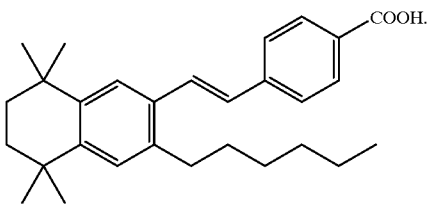

Formula VII

13. The method of claim 2, wherein the RAR agonist is a compound of Formula VIII:

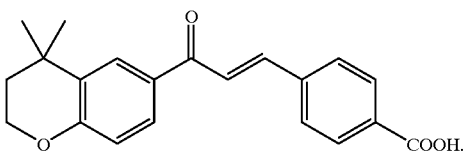

Formula VIII

14. A method of treating a disease associated with alveolar damage in a mammal comprising administering to the mammal an RAR agonist that is at least gamma selective and is RARα sparing.

15. The method of claim 14 wherein the RAR agonist is an RAR γ/β selective agonist.

16. The method of claim 14 wherein the RAR agonist is an RARγ selective agonist.

17. The method of claim 16, wherein the RARγ selective agonist binds to the RARγ receptor and transactivates with an EC$_{50}$ of at least 200 nM.

18. The method of claim 16, wherein the selectivity of the RARγ selective agonist for the RARγ receptor at least 20 fold relative to the RARα and RARβ receptors.

19. The method of claim 16, wherein the RAR agonist is selected from compounds of Formula I:

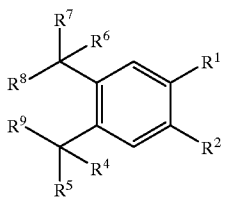

Formula I where R[1] is a residue of the formula

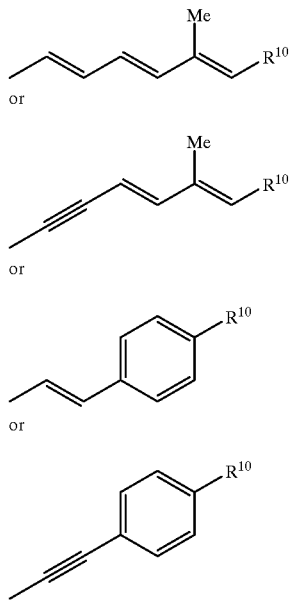

R[2] is C$_2$–C$_8$ alkanoyl, C$_2$–C$_8$ alkyl, C$_2$–C$_8$ alkenyl, C$_2$–C$_8$ alkynyl or —OCH$_2$R[3];

R[3] is hydrogen, C$_1$–C$_6$ alkyl, C$_2$–C$_6$ alkenyl or C$_2$–C$_6$ alkynyl;

R[4] to R[9] are each independently hydrogen or C$_1$–C$_6$ alkyl; or R[8] and R[9] together are (CR$^a$R$^b$)$_n$, R$^a$ and R$^b$ are independently hydrogen or C$_1$–C$_6$ alkyl, n is 1, 2 or 3 and R[4] to R[7] are the same as above;

R[10] is carboxyl, C$_{1-6}$ alkoxycarbonyl or mono- or di-(C$_{1-6}$ alkyl)carbamoyl; and their pharmaceutically acceptable salts.

20. The method of claim 16 wherein the RAR agonist is selected from compounds of Formula II:

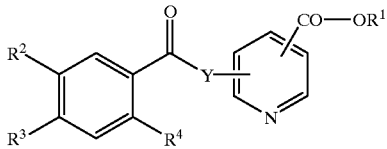

Formula II wherein;

R[1] is hydrogen or C$_1$–C$_6$ alkyl;

R[2] is C$_1$–C$_6$ alkyl or adamantyl;

R[3] is C$_1$–C$_6$ alkyl or hydroxy; or

R[2] and R[3] taken together are —(CR[6]R[7])$_n$— (where R[6] and R[7] are hydrogen or C$_1$–C$_6$ alkyl and n is 3, 4 or 5);

$R^4$ is $C_2$–$C_8$ alkanoyl, $C_2$–$C_8$ alkyl, $C_2$–$C_8$ alkenyl, $C_2$–$C_8$ alkynyl or —$OCH_2R^5$;

$R^5$ is $C_1$–$C_6$ alkyl, $C_2$–$C_6$ alkenyl or $C_2$–$C_6$ alkynyl;

Y is oxygen or sulfur; and their pharmaceutically acceptable salts.

21. The method of claim 16, wherein the RAR agonist is selected from compounds of Formula III:

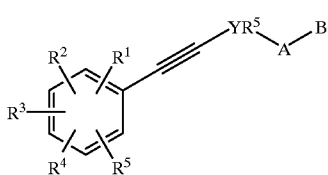

Formula III wherein $R^1$–$R^3$ and $R^5$ are independently hydrogen, lower alkyl of 1 to 6 carbons, branched chain alkyl or cycloalkyl of 3 to 15 carbons, lower alkyl substituted cycloalkyl of 3 to 15 carbons;

$R^4$ is lower alkyl of 1 to 6 carbons, branched chain alkyl or cycloalkyl of 3 to 15 carbons, or lower alkyl substituted cycloalkyl of 3 to 15 carbons;

X is S or O;

Y is a phenyl group, or heteroaryl selected from a group consisting of pyridyl, thienyl, furyl, pyridazinyl, pirimidinyl, pyrazinyl, thiazolyl, imidazolyl, and oxazolyl, said groups being substituted with the R5 group defined above;

A is $(CH_2)_n$, where n is 0 to 5, lower branched chain alkyl having 3 to 6 carbons, cycloalkyhl having 3 to 6 carbons, alkenyl having 2 to 6 carbons and 1 or 2 double bonds, alkynyl having 2 to 6 carbons and 1 or 2 triple bonds;

B is hydrogen, COOH or a pharmacetically acceptable salt thereof, $COOR^8$, $CONR^9R^{10}$, —$CH_2OH$, $CH_2OR^{11}$, $CH_2OCOR^{11}$, CHO, $CH(OR^{12})_2$, $CHOR^{13}O$, —$COR^7$, $CR^7(OR^{12})_2$, or $CR^7OR^{13}O$, where $R^7$ is an alkyl, cycloalkyl, or alkenyl group containing 1 to 5 carbons, $R^8$ is an alkyl group of 1 to 10 carbons, or a cycloalkyl group of 5 to 10 carbons, or $R^8$ is phenyl or lower alkylphenyl, $R^9$ and $R^{10}$ independently are hydrogen, an alkyl grop of 1 to 10 carbons, or a cycloalkyl group of 5 to 10 carbons, or phenyl or lower alkylphenyl, $R^{11}$ is a lower alkyl, phenyl or lower alkylphenyl, $R^{12}$ is lower alkyl, and $R^{13}$ is divalent alkyl radical of 2 to 5 carbons.

22. The method of claim 16 wherein the RAR agonist is selected from compounds of Formula IV:

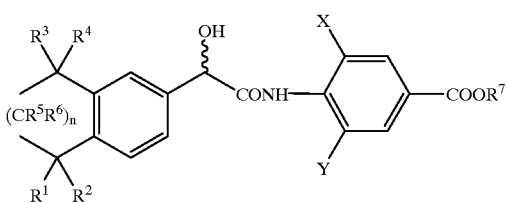

Formula IV wherein

X is F, Cl, OH, or $CH_3$;

Y is H or F;

$R^1$ through $R^6$ are each independently hydrogen or $C_1$ to $C_6$ alkyl;

n is an integer of 1 to 4; and $R^7$ is hydrogen or a carboxyl-protecting group;

and pharmaceutically acceptable salts thereof.

23. The method of claim 16, wherein the RAR agonist is selected from compounds of Formula V

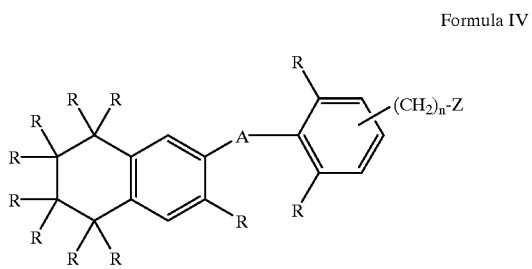

Formula IV wherein the R groups are independently hydrogen or lower alkyl;

A is —C(O)O—, —OC(O)—, —C(O)S—, or SC(O)—;

n is 0 to 5; and

Z is H, —COB, —OE, —CHO or an acetal derivative thereof, or —$COR^3$ wherein

B is —$OR^1$ wherein $R^1$ is an ester-forming group, or B is —$N(R)_2$ wherein R is hyrogen or lower alkyl;

E is hydrogen, an ether-forming group, or —$COR^2$ where $R^2$ is hydrogen, lower alkyl, phenyl, or lower alkyl phenyl;

$R^3$ is —$(CH_2)_mCH_3$ wherein m is 0 to 4 and the sum of n and m does not exceed 4.

24. The method of claim 16, wherein the RAR agonist is selected from compounds of Formula VI

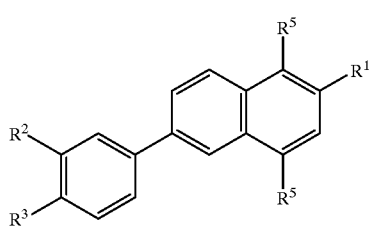

Formula VI wherein $R^1$ is $C(O)R^6$ or $CH_2OH$ (where $R^6$ is hydroxy or $C_1$–$C_6$ alkoxy);

$R^2$ is hydrogen $C_1$–$C_{15}$ alkyl, $C_1$–$C_6$ alkoxy or cycloaliphatic;

$R^3$ is hydrogen, hydroxy, $C_1$–$C_6$ alkyl, dihydroxy $C_1$–$C_6$ alkyl, $C_1$–$C_{10}$ alkoxy or cycloaliphatic; and $R^4$ and $R^5$ are independently hydrogen, hydroxy, $C_1C_6$ alkyl, $C_1$–$C_6$ alkoxy.

25. The method of claim 19, wherein the RAR agonist is a compound of Formula VII:

Formula VII

26. The method of claim 15, wherein the RAR agonist is a compound of Formula VIII:

Formula VIII

27. The method of claim 1, wherein said mammal is a human.
28. The method of claim 27, wherein the RAR agonist is an RARγ/β selective agonist.
29. The method of claim 27, wherein the RAR agonist is an RARγ selective agonist.
30. The method of claim 29, wherein the RAR selective agonist binds to the RARγ receptor and transactivates with an $EC_{50}$ of at least 200 nM.
31. The method of claim 29, wherein the selectivity of the RARγ selective agonist for the RARγ receptor is at least 20 fold relative to the RARα and RARβ receptors.
32. The method of claim 29, wherein the RAR agonist is selected from compounds of Formula I:

Formula I where $R^1$ is a residue of the formula or or

-continued or $R^2$ is $C_2$–$C_8$ alkanoyl, $C_2$–$C_8$ alkyl, $C_2$–$C_8$ alkenyl, $C_2$–$C_8$ alkynyl or $-OCH_2R^3$;
$R^3$ is hydrogen, $C_1$–$C_6$ alkyl, $C_2$–$C_6$ alkenyl or $C_2$–$C_6$ alkynyl;
$R^4$ to $R^9$ are each independently hydrogen or $C_1$–$C_6$ alkyl; or $R^8$ and $R^9$ together are $(CR^aR^b)_n$, $R^a$ and $R^b$ are independently hydrogen or $C_1$–$C_6$ alkyl, n is 1, 2 or 3 and $R^4$ to $R^7$ are the same as above;
$R^{10}$ is carboxyl, $C_{1-6}$ alkoxycarbonyl or mono- or di-($C_{1-6}$alkyl)carbamoyl; and their pharmaceutically acceptable salts.

33. The method of claim 29, wherein the RAR agonist is selected from compounds of Formula II:

Formula II wherein:
$R^1$ is hydrogen or $C_1$–$C_6$ alkyl;
$R^2$ is $C_1$–$C_6$ alkyl or adamantyl;
$R^3$ is $C_1$–$C_6$ alkyl or hydroxy; or
$R^2$ and $R^3$ taken together are $-(CR^6R^7)_n-$ (where $R^6$ and $R^7$ are hydrogen or $C_1$–$C_6$ alkyl and n is 3, 4 or 5);
$R^4$ is $C_2$–$C_8$ alkanoyl, $C_2$–$C_8$ alkyl, $C_2$–$C_8$ alkenyl, $C_2$–$C_8$ alkynyl or $-OCH_2R^5$;
$R^5$ is $C_1$–$C_6$ alkyl, $C_2$–$C_6$ alkenyl or $C_2$–$C_6$ alkynyl;
Y is oxygen or sulfur; and their pharmaceutically acceptable salts.

34. The method of claim 29, wherein the RAR agonist is selected from compounds of Formula III:

Formula III wherein
$R^1$–$R^3$ and $R^5$ are independently hydrogen, lower alkyl of 1 to 6 carbons, branched chain alkyl or cycloalkyl of 3 to 15 carbons, lower alkyl substituted cycloalkyl of 3 to 15 carbons;
$R^4$ is lower alkyl of 1 to 6 carbons, branched chain alkyl or cycloalkyl of 3 to 15 carbons, or lower alkyl substituted cycloalkyl of 3 to 15 carbons;
X is S or O;
Y is a phenyl group, or heteroaryl selected from a group consisting of pyridyl, thienyl, furyl, pyridazinyl, pirimidinyl, pyrazinyl, thiazolyl, imidazolyl, and oxazolyl, said groups being substituted with the R5 group defined above;

A is $(CH_2)_n$ where n is 0 to 5, lower branched chain alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds;

B is hydrogen, COOH or a pharmacetically acceptable salt thereof, $COOR^8$, $CONR^9R^{10}$, $-CH_2OH$, $CH_2OR^{11}$, $CH_2OCOR^{11}$, CHO, $CH(OR^{12})_2$, $CHOR^{13}O$, $-COR^7$, $CR^7(OR^{12})_2$, or $CR^7OR^{13}O$, where $R^7$ is an alkyl, cycloalkyl, or alkenyl group containing 1 to 5 carbons, $R^8$ is an alkyl group of 1 to 10 carbons, or a cycloalkyl group of 5 to 10 carbons, or $R^8$ is phenyl or lower alkylphenyl, $R^9$ and $R^{10}$ independently are hydrogen, an alkyl grop of 1 to 10 carbons, or a cycloalkyl group of 5 to 10 carbons, or phenyl or lower alkylphenyl, $R^{11}$ is a lower alkyl, phenyl or lower alkylphenyl, $R^{12}$ is lower alkyl, and $R^{13}$ is divalent alkyl radical of 2 to 5 carbons.

35. The method of claim 29, wherein the RAR agonist is selected from compounds of Formula IV:

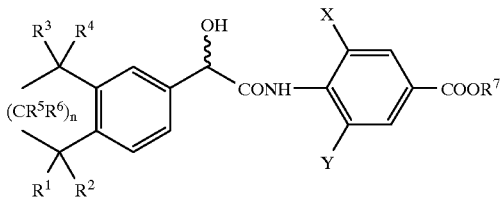

Formula IV wherein
X is F, Cl, OH, or $CH_3$;
Y is H or F;
$R^1$ through $R^6$ are each independently hydrogen or $C_1$ to $C_6$ alkyl;
n is an integer of 1 to 4; and
$R^7$ is hydrogen or a carboxyl-protecting group; and pharmaceutically acceptable salts thereof.

36. The method of claim 29, wherein the RAR agonist is selected from compounds of Formula V

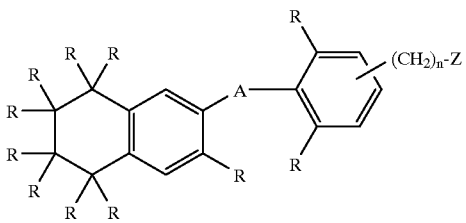

Formula V wherein
the R groups are independently hydrogen or lower alkyl;
A is $-C(O)O-$, $-OC(O)-$, $-C(O)S-$, or $SC(O)-$;
n is 0 to 5; and
Z is H, $-COB$, $-OE$, $-CHO$ or an acetal derivative thereof, or $-COR^3$ wherein
  B is $-OR^1$ wherein $R^1$ is an ester-forming group, or B is $-N(R)_2$ wherein R is hydrogen or lower alkyl;

E is hydrogen, an ether-forming group, or $-COR^2$ where $R^2$ is hydrogen, lower alkyl, phenyl or lower alkyl phenyl;
$R^3$ is $-(CH_2)_mCH_3$ wherein m is 0 to 4 and the sum of n and m does not exceed 4.

37. The method of claim 29, wherein the RAR agonist is selected from compounds of Formula VI

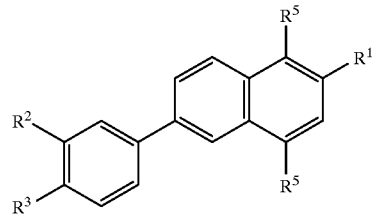

Formula VI wherein
$R^1$ is $C(O)R^6$ or $CH_2OH$ (where $R^6$ is hydroxy or $C_1$–$C_6$ alkoxy);
$R^2$ is hydrogen $C_1$–$C_{15}$ alkyl, $C_1$–$C_6$ alkoxy or cycloaliphatic;
$R^3$ is hydrogen, hydroxy, $C_1$–$C_6$ alkyl, dihydroxy $C_1$–$C_6$ alkyl, $C_1$–$C_{10}$ alkoxy or cycloaliphatic; and
$R^4$ and $R^5$ are independently hydrogen, hydroxy, $C_1C_6$ alkyl, $C_1$–$C_6$ alkoxy.

38. The method of claim 32, wherein the RAR agonist is a compound of Formula VII:

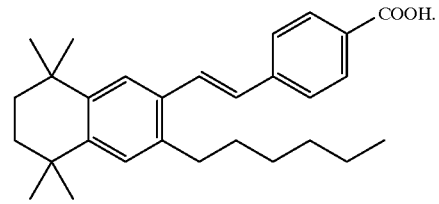

Formula VII

39. The method of claim 28, wherein the RAR agonist is a compound of Formula VIII:

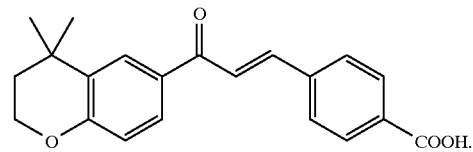

Formula VIII

40. The method of claim 14, wherein said mammal is a human.

41. The method of claim 40 wherein the RAR agonist is an RAR γ/β selective agonist.

42. The method of claim 40 wherein the RAR agonist is an RARγ selective agonist.

43. The method of claim 42, wherein the RARγ selective agonist binds to the RARγ receptor and transactivates with an $EC_{50}$ of at least 200 nm.

44. The method of claim 42, wherein the selectivity of the RARγ selective agonist for the RARγ receptor at least 20 fold relative to the RARα and RARβ receptors.

* * * * *